Figure 1:
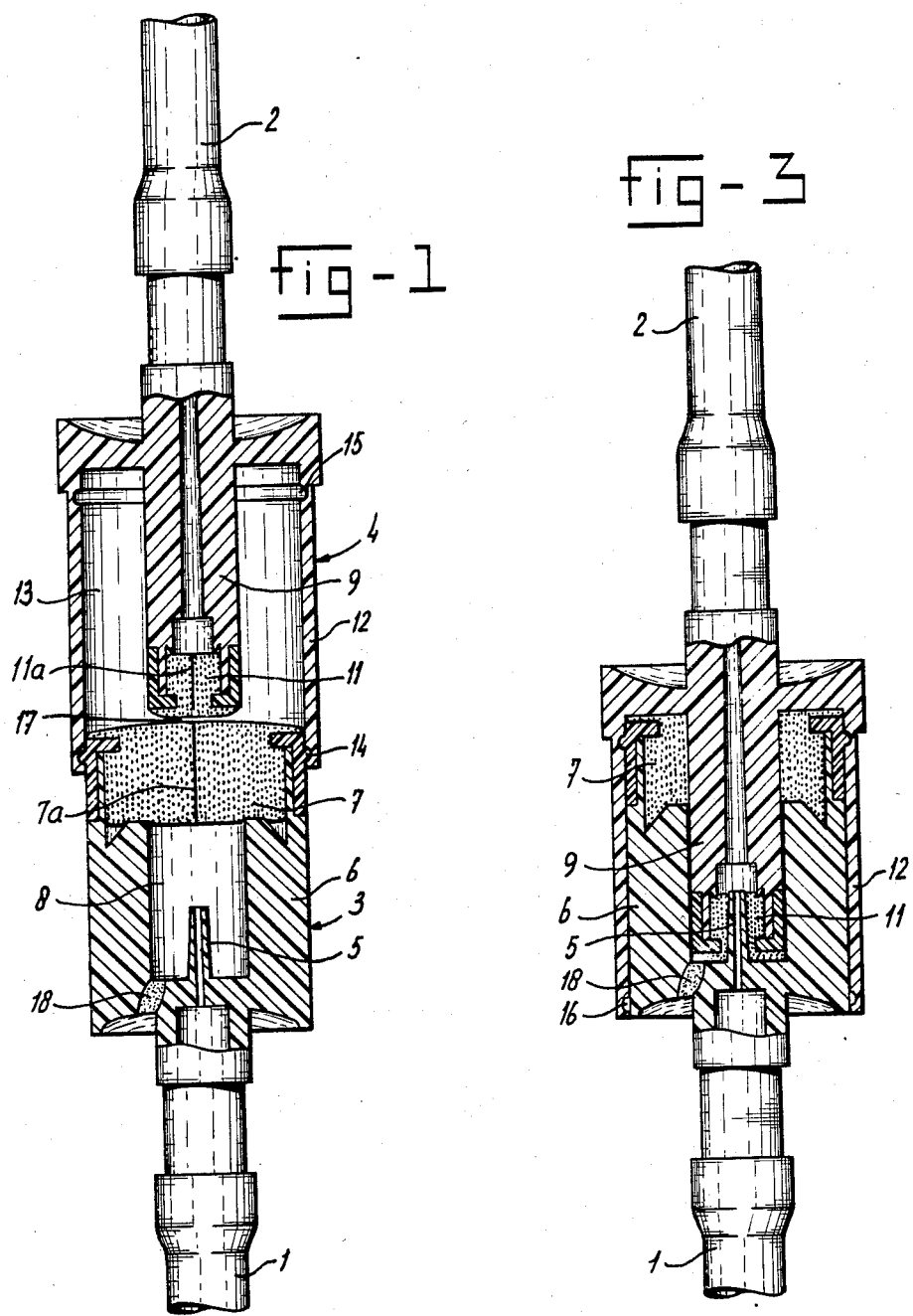

United States Patent [19]

Wolff-Mooij

[11] Patent Number: 4,610,469
[45] Date of Patent: Sep. 9, 1986

[54] CONNECTOR ASSEMBLY FOR STERILE CONNECTION OR TWO INTERNALLY STERILE CONTAINERS OF TUBINGS

[75] Inventor: Marcelle N. Wolff-Mooij, Ridderkerk, Netherlands

[73] Assignee: Steritech B.V., Ridderkerk, Netherlands

[21] Appl. No.: 575,325

[22] Filed: Jan. 31, 1984

[30] Foreign Application Priority Data

Feb. 2, 1983 [NL] Netherlands ............... 8300386

[51] Int. Cl.⁴ .................................... F16L 31/00
[52] U.S. Cl. ................................ 285/260; 285/3;
285/901; 251/149.1; 251/149.7; 251/149.9;
604/411; 604/905
[58] Field of Search ............... 285/3, 4, DIG. 2, 260;
604/411, 414, 905, 249, 33; 251/149.1, 149.7,
149.9

[56] References Cited

U.S. PATENT DOCUMENTS

| | | | |
|---|---|---|---|
| 3,986,508 | 10/1976 | Barrington | 285/3 X |
| 4,022,205 | 5/1977 | Tenczar | 285/3 X |
| 4,030,494 | 6/1977 | Tenczar | 285/423 X |
| 4,143,853 | 3/1979 | Abramson | 251/149.1 |
| 4,161,949 | 7/1979 | Thanawalla | 604/411 |
| 4,334,551 | 6/1982 | Pfister | |
| 4,431,424 | 2/1984 | Svensson | 604/33 |
| 4,508,367 | 4/1985 | Oreopoulos et al. | 285/3 |
| 4,511,359 | 4/1985 | Vaillancourt | 285/3 X |

FOREIGN PATENT DOCUMENTS 2452858 5/1975 Fed. Rep. of Germany .
2407417 5/1979 France .
6505766 11/1966 Netherlands .
2067075 10/1980 United Kingdom ............... 604/905

Primary Examiner—Richard J. Scanlan, Jr.
Assistant Examiner—Sherish A. Desai
Attorney, Agent, or Firm—Weiser & Stapler

[57] ABSTRACT

A connector assembly for sterile connection of two internally sterile containers or tubings comprises two connectors (3, 4). The first connector (3) has a male part (5) inside a housing (6), a connecting device to connect the first connector to a first container or tubing (1), a first deformable barrier (7) spaced from the male part (5) and a chamber (8) between the male part (5) and the first barrier (7). The second connector (4) comprises a female part (9), a connecting device to connect the second connector to a second container or tubing (2) and a second deformable barrier (11) closing the female part (9). In connecting the connectors (3, 4) first both deformable barriers (7, 11) are brought into contact with each other after which the male part (5) of the first connector (3) is put through the second barrier (11) closing the female part (9) of the second connector (4). To guarantee that during each coupling and disconnecting procedure the absolute sterility of the interior of the female part is maintained, the second barrier (11) is mounted in the entrance part of the female part (9) and is pushed entirely through the first barrier (7) during the connection of the connectors (3, 4) into the chamber (8) between the male part (5) and the first barrier (7) before the male part (5) can penetrate the second barrier (11). Further at least the second barrier (11) consists of a resilient material which during the disconnecting procedure of the connectors will be restored in the chamber (8) into the original closing position.

9 Claims, 3 Drawing Figures

CONNECTOR ASSEMBLY FOR STERILE CONNECTION OR TWO INTERNALLY STERILE CONTAINERS OF TUBINGS

The invention relates to a connector assembly for sterile connection of two internally sterile containers or tubings comprising a first connector having a male part mounted inside a housing, a connecting device to connect the first connector with a first container or tubing, a deformable barrier situated in front of the male part, and a chamber between the male part and the first barrier, and a second connector having a female part, a connecting device to connect the second connector with a second container or tubing, and a second deformable barrier closing a female part, so that in connecting the connectors both deformable barriers are first brought into contact after which the male part of the first connector is put through the second barrier closing the female part of the second connector.

Such an assembly is disclosed in U.S. Pat. No. 4,030,494 (=DE-A-2 452 858).

In medical care, in medical, biological and pharmaceutical research and in the pharmaceutical industry it is often important that not any bacterium or other infectious agent (yeast, fungus, virus) and hardly any disinfection liquid penetrates into a system of mutually connected units (tubings, bottles, containers, catheters, infusion means, drains). Up to now, one did not quite meet these conditions. In certain cases this can have serious consequences. During chronic ambulatory peritioneal dialysis (CAPD) a certain quantity of sterile dialysis fluid is brought from a plastic bag through a tubing system into the abdominal cavity. After a period of some hours the fluid is transferred from the abdominal cavity back into the bag. In the meantime an osmotic equilibrium is accomplished between the waste substances accumulated in the blood of the uraemic patient and the dialysis fluid. By replacing the dialysis fluid by fresh dialysis fluid after for instance six hours, one removes again and again a portion of the accumulated waste substances from the blood. As the dialysis fluid is changed four to five times a day, about 1500 connections and disconnections of dialysis bags are necessary per year. It is absolutely necessary to carry out a sterile connecting and disconnecting procedure. Since the dialysis fluid does not comprise white blood cells, it is clear that any infectious agents i.e. bacteria introduced during the connecting procedure, even if there are very few, may multiply unhindered inside the abdominal cavity of the patient. If for instance per coupling about one tenth of a milliliter of air arrives in the dialysis system connected with the abdominal cavity, this would mean that with 150 connections and disconnections, 150 milliliter of air would arrive in the system. The concentration of bacteria in the air is variable but may amount for normally clear air from approximately 0.2 to about 5 per 100 milliliter. This means that there is a very big chance that one or more bacteria will enter one or more times a year, together with the air through the dialysis system, into the abdominal cavity. This is in accordance with the practice of CAPD according to which about 60% of the patients suffer from peritonitis within two years after starting this kind of treatment. In most cases the bacteria or infections agents normally present in the air can be found in the dialysis fluid. In view of the fact that the treatment takes place at home where the patients themselves will carry out the replacements and actions, a simple system is necessary which must, however, give 100% security. Any contact of the connectors with the hand or clothing should not give rise to contamination of the dialysis fluid. No new infectious agents should be allowed to penetrate after the disinfection procedure of the exterior. In addition it is of essential importance that an effective protection against contamination during the disconnection of the connectors is found.

Also in cases it seems it does not matter whether germs or desinfectant enters into the system, it is desirable that this is limited to a minimum. If infectious agents are introduced into the bloodstream during the administration of intravenous fluids or medication, they normally come into contact with $10^7$ white blood cells per milliliter of blood which strongly counteracts their multiplication. However, there is a considerable number of patients suffering from a serious reduction of the number or immunological activity of the white blood cells (for instance during the treatment of some cancer patients or acquired immune deficiency patients). The introduction of one single bacterium in the body of these groups of patients can cause perilous infections.

Up to now one can distinguish mainly three types of connector assemblies. Not one of these types meets the condition that not any infectious agent is allowed to penetrate the tubings or containers to be connected. In a first type of connector assembly the female part is closed by a membrane. To achieve the connection the male part, not covered by a barrier, will bring a small quantity of non-sterile air into the tubings to be connected, while a small but non neglectable quantity of germedical fluid will enter the tubings each time, when, as is usually done, both connectors are sprayed with it. The consequences of this are explained above. Examples of this first type of connector assemblies are disclosed among others in CA-A- 1 105 959 and GB-A-2 067 075.

In a second type of connector assembly both connectors are provided with a deformable barrier and before connecting these connectors the barriers are first brought into contact with each other, after which the fixation points of these barriers will not change their mutual position. One of the connectors comprises a telescopically movable penetration tube which during the coupling of the connectors is pushed through both barriers and is slid with its front end into the other connector. An example of this type of connector assembly is disclosed in U.S. Pat. No. 4,334,551. In coupling the connectors a sterile connection might be achieved if both barriers would have been sprayed before hand with a sterilizing liquid, however, there is the risk that the penetration tube after penetrating the first barrier, pushes away the second barrier and unsterile air would be sucked into the space created between both barriers. However a much more serious drawback is that during the disconnection procedure the barriers are pulled loose from each other by the retracting penetration tube so that unsterile air is sucked between both barriers which air could contaminate the outside of the penetration tube. In addition vacuum will be generated in a connector if the penetration tube is pulled back from that connector, so that unsterile air could be sucked into the connector and between the closing slit of the deformable barrier. This would mean that precisely the connector meant for multiple use would not be sterile anymore. In any case it is apparent that both deformable barriers close in non-sterile air during the disconnecting procedure. This may lead to the presence of infectious agents in between the slits of the barriers. Finally, in this type of connector assembly with a movable penetration tube, it is of essential importance for the achievement of a sterile connection that the movement of the penetration tube is accurately axial with respect to both connector axis. In practice this will not always be the case.

A third type of connector assembly is indicated in the preamble and is disclosed among others in U.S. Pat. No. 4,030,494 already mentioned. This known assembly is not suitable for multiple use because the barriers are torn during the coupling procedure or are broken in another way and would remain open during the disconnecting procedure. The fixation points of the barriers remain next to each other during the coupling procedure in this type too.

It is an object of the invention to provide a connector assembly indicated in the preamble of which at least the connector provided with female part is suitable for multiple use and whereby during each coupling and disconnecting procedure the absolute sterility of the interior of the female part is guaranteed.

According to the invention the connector assembly indicated in the preamble is characterized by the fact that said second barrier is mounted at the entrance of the female part and during the coupling procedure of the connectors is pushed through said first barrier into said chamber between the male part and said first barrier before the male part can penetrate through said second barrier, and that at least the second barrier consists of a resilient material which, during the disconnection procedure of the connectors, is restored into the original closed condition inside said chamber.

In the construction of the present new type of connector assembly it is of essential importance that during the coupling procedures of the connectors the barrier of the female part is opened by the male part only after this barrier is completely introduced into a closed sterile chamber, while during the disconnecting procedure the retraction of the male part out of the barrier of the female part and the closing of this barrier, takes place inside a sterile chamber. Non-sterile air is absolutely prevented from entering into the female part. The tubing of the connector belonging to this female part can remain connected to the human body without the risk that infectious agents could enter into the tubing system during the coupling of a new sterile connector provided with a male part to the connector of the female part.

Before the connection is accomplished, both parts to be connected are sprayed with a disinfection liquid. The barriers of male parts and female parts will be brought into contact betweem them. The barriers will then remain in this condition long enough (for instance 2 minutes) to kill the germs on the barriers. The penetration of any unsterile air into the chambers to be connected is excluded by the application of two barriers to be brought into contact with each other, while only a portion of the very thin film of disinfection liquid and consequently a negligible amount of it will enter into the tubing system.

The first barrier also consists of a resilient material that after being penetrated by the female part, behaves as a water and air tight closure ring around this female part. Thus, unsterile air is prevented from entering into said chamber behind the first barrier. During the disconnection procedure of the connectors this barrier will be restored in the original closing condition.

Starting from a construction in which the house of the first connector slides telescopically along the house of the second connector, it is preferred that both houses are provided with cooperating positioning members for the fixation of a position in which the barriers are kept at a very small distance with respect to each other. The barriers, previously sprayed with disinfection fluid, may then be kept in this position long enough to achieve the killing of infectious agents on said barriers.

A fixation of the mutual position of both connectors may also be useful in the final position, in which the connecting procedure is completed. Therefore both houses are provided with co-operating positioning members for fixation of a position in which the male part retains its final position in the female parts.

There are several possibilities for the positioning members. The most simple possibility is a thread on both houses whereby the germicidal position coincides with the position in which the threads of both houses are in touch with each other but do not mesh into each other, whereas the connecting position coincides with the position in which one house is screwed up on the other. However, it is preferred that the positioning members consist of snap members.

Yet another possibility is that the positioning members consist of a double bayonet coupling.

The invention will now be elucidated with the aid of the figures showing an example.

Figure 2:
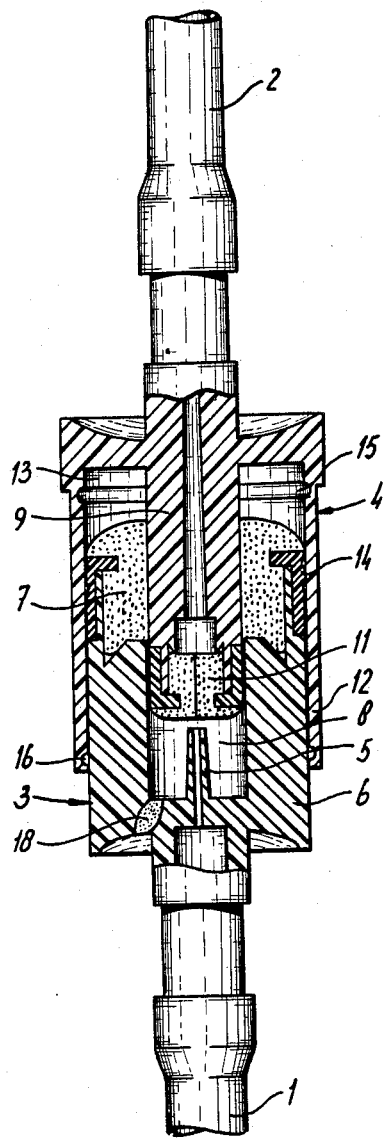

FIGS. 1, 2 and 3 are cross-sections of the connector assembly showing respectively the starting position, an intermediate position and the entirely coupled position.

The connector assembly shown is meant for accomplishing a sterile connection of two tubings 1,2. The assembly comprises two connectors 3 and 4 which are connected in the usual way with a sterile tubing. The connector 3 includes a male part 5 provided with a channel, a house 6 and a barrier 7 connected at the front part of that house and made of resilient material such as foamed or non-foamed elastic plastic material. A certain distance exists between the end of the male part 5 and the barrier 7 so that a chamber 8 is confined within the connector 3. The connector 4 includes a female part 9 provided with a channel, a barrier 11 positioned at the front part of it and also made of elastic deformable material such as a foamed or non-foamed block of elastic plastic material, and a house 12. An annular space 13 is present between the house 12 and the female part 9.

A snap member 14 is positioned adjacent to the front edge of the house 6 of the connector 3 said snap member being able to co-operate with complementary shaped snap members 15, 16 of the connector 4 to fix both connectors in positions to be described later.

To connect both connectors which are internally sterile, in an absolutely sterile way, the barriers 7 and 11 and the space 13 are sprayed with a disinfectant. Then, the connectors are brought in the position according to FIG. 1, in which snap members 14 and 16 co-operate. In this position the barriers 7 and 11 are so close that a liquid film 17 of capillary thickness is present in between them. This starting position is maintained during about two minutes, sufficient to kill the bacteria, fungi or virus. Then the connectors are moved toward each other. The closed barrier 11 of female part 9 then penetrates the barrier 7 of connector 3, coming into the sterile chamber 8; this position is indicated in FIG. 2. The male part 5 will after that penetrate the female part 9 by further pushing the connectors into each other, which position is shown in FIG. 3. The purpose of chamber 8 is to take up barrier 11 and a portion of the female part 9. Preferably chamber 8 is connected with the exterior by a channel 18 provided with a bacterial filter. During the disconnection of the connectors no negative pressure will exist in chamber 8 while only sterile air will have arrived through the bacterial filter in channel 18 into chamber 8. It is not excluded that chamber 8 is entirely or partially filled with deformable material which is compressed when the female part penetrates chamber 8. The final position according to FIG. 3 is fixed by the co-operating snap members 14, 15 or other positioning members. It will be clear that during the connection of the connectors the barrier 11 is only opened after it has entirely entered into the closed sterile chamber 8. In reverse order, the barrier 11 will be able to close completely while still inside the closed sterile chamber 8 before leaving the connector 3 through the split barrier 7 when the connectors are disconnected.

In connecting the connectors 3, 4 no air from outside can penetrate inside the tubings 1 and 2. The capillary liquid film 17 of disinfection fluid is squeezed away during the connection procedure so that at the most a negligible adhered quantity of disinfection fluid will enter chamber 8. No unsterile air can enter the female part 9 during the disconnection procedure because the barrier 7 will close air tight around the female part 9 so that unsterile air is prevented from entering chamber 8 and because the barrier 11 closes inside the sterile chamber 8.

As a consequence of the application of two barriers 7 and 11 which at the start of the connecting procedure are in touch with each other and of which one barrier 11 penetrates the other barrier 7 thereby entering a sterile chamber 8, an absolutely sterile connection is achieved. To entirely prevent contact between the wall of the channel of the male part 5 with the barrier 11 of the female part 9, the male part can be provided with a setting fitting around the protruding end of a small pipe introduced in the channel of the female part. By this measure even the very thin film of disinfection liquid is prevented from contacting the female part.

Several modifications of the shown and described connector assembly are possible within the scope of the invention. For instance one of the connectors can be a closing cap of a container such as a glass or plastic bottle, tube or syringe. Also the connector including the female part could be the upper half of an infusion drip chamber having built in de-aeration means, whereas the connector comprising the male part is the closing cap of an infusion bottle. However, the following aspects are essential for the invention:
 both connectors have a deformable elastic barrier which at the start of the connection of the connectors are in touch with each other to squeeze air and disinfection liquid aside,
 the deformable barrier of the female part can only be opened by the male part after that barrier has penetrated the barrier of the male part and after having come into a sterile chamber,
 at least the barrier of the female part consists of a material which after being opened can take its original closing position.

In the case of accidental disconnection one encounters no risk of contamination of the system, as a consequence of the fact that the barrier of the female part will be closed automatically upon retraction of the male part. In fact it is possible that a dialysis patient walks around with the peritoneal dialysis catheter being closed by means of a connector having a female connector. This is contrary to the usual situation where as a consequence of the risk of infection during the connection procedures, the patient remains continuously connected to the dialysis container.

The contamination of the female part is excluded because the opening and closing of the deformable barrier of the female part always takes place in a sterile chamber. The connector, to which the female part belongs, is suitable for mutliple use and can be kept in connection with the human body through a tubing for a long time. In some cases it is desirable that one or both barriers are entirely, or at least partially split, as shown for example in FIG. 1 wherein the barrier 7 is split at 7a, and the barrier 11 is split at 11a. However, while preferred, this is not always necessary. Further it is an advantage that the connectors do not have a movable penetration tube. This makes the construction simpler and less vulnerable for a non-accurate connecting procedure as well as for contaminations.

The houses have a mechanical protection function as well as a positioning function. The houses also play a roll in preventing the introduction of contaminants after the connectors are connected with each other. When the connectors are not connected with each other, both connector houses may be protected by a cap fitting over the houses, preventing the connectors against dust or other impurities. Further these caps protect the barriers mechanically.

I claim:
1. In a connector assembly for sterile connection of two internally sterile containers or tubings, comprising:
 a first connector having a male part inside a housing, a connecting device to connect said first connector to a first container or tubing, and a first deformable barrier spaced from the male part to define a chamber between said male part and said first barrier, and
 a second connector having a female part, a connecting device to connect said second connector to a second container or tubing, and a second deformable barrier closing the female part,
 wherein by connecting said first and second connectors, both of said deformable barriers are brought into contact with each other so that the male part of the first connector is pushed through the second barrier, closing the female part of the second connector,
 the improvement wherein said second barrier is mounted in the female part so that said second barrier is pushed entirely through said first barrier during the connection of said first and second connectors, and into the chamber between said male part and said first barrier, before the male part can penetrate said second barrier, and wherein at least the second barrier is comprised of a resilient material which during disconnection of said first and second connectors is restored in said chamber in the original, closing condition.

2. The connector assembly of claim 1, wherein the first barrier is also comprised of a resilient material which behaves as an air tight closure ring around the female part when the female part is pushed through the first barrier, and which is restored in the original, closing condition during said disconnection of the first and second connectors.

3. The connector assembly of claims 1 or 2, wherein a housing associated with the first connector is mounted to slide telescopically along a housing associated with the second connector, and wherein said housings are provided with cooperating positioning members for fixing a first position in which a very small distance is maintained between the barriers.

4. The connector assembly of claim 3, wherein said housings are provided with cooperating positioning members for fixing a second position in which the male part takes its final position in the female part.

5. The connector assembly of claim 4, wherein the positioning members are snap members.

6. The connector assembly of claim 4, wherein the positioning members are a double bayonet closure.

7. The connector assembly of claim 3, wherein the positioning members are snap members.

8. The connector assembly of claim 3, wherein the positioning members are a double bayonet closure.

9. The connector assembly of claim 1, wherein the chamber of the first connector communicates with the exterior through a channel provided with a bacterial filter.

* * * * *